United States Patent [19]

Lungershausen et al.

[11] 4,418,146

[45] Nov. 29, 1983

[54] PREPARATION OF D-N-CARBAMYL-α-AMINOACIDS AND MICRO-ORGANISMS FOR CARRYING OUT THIS PREPARATION

[75] Inventors: Rolf Lungershausen, Ludwigshafen; Christoph Martin, Mannheim; Stefan Marcinowski, Ludwigshafen; Hardo Siegel, Speyer; Werner Kuesters, Ludwigshafen, all of Fed. Rep. of Germany

[73] Assignee: BASF Aktiengesellschaft, Ludwigshafen, Fed. Rep. of Germany

[21] Appl. No.: 287,697

[22] Filed: Jul. 28, 1981

[30] Foreign Application Priority Data

Aug. 18, 1980 [DE] Fed. Rep. of Germany ....... 3031151

[51] Int. Cl.³ .................. C12P 13/04; C12N 9/78; C12N 1/20
[52] U.S. Cl. .................................... 435/106; 435/227; 435/253
[58] Field of Search .............. 435/106, 280, 253, 227

[56] References Cited

U.S. PATENT DOCUMENTS

| | | | |
|---|---|---|---|
| 3,964,970 | 6/1976 | Dinelli et al. | 435/280 |
| 4,094,741 | 6/1978 | Yamada et al. | 195/29 |
| 4,111,749 | 9/1978 | Degen et al. | 435/280 |
| 4,211,840 | 7/1980 | Nakamori et al. | 435/107 |
| 4,237,227 | 12/1980 | Yamada et al. | 435/108 |
| 4,248,967 | 2/1981 | Viglia et al. | 435/106 |

FOREIGN PATENT DOCUMENTS 2019835 11/1979 United Kingdom .
2042531 9/1980 United Kingdom .

*Primary Examiner*—Lionel M. Shapiro
*Attorney, Agent, or Firm*—Keil & Witherspoon

[57] ABSTRACT

A process for the preparation of D-carbamyl-α-aminoacids of the formula

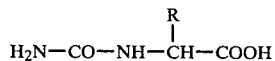

where R has the meanings given in the description, by enzymatic cleavage of the corresponding hydantoins by means of thermophilic, non-sporulating hydantoin-cleaving micro-organisms or of extracts therefrom.

5 Claims, No Drawings

PREPARATION OF D-N-CARBAMYL-α-AMINOACIDS AND MICRO-ORGANISMS FOR CARRYING OUT THIS PREPARATION

The present invention relates to a process for the preparation of D-N-carbamyl-α-aminoacids from hydantoins, and to microorganisms for carrying out this preparation.

D-N-carbamyl-α-aminoacids are important intermediates for the preparation of D-aminoacids which in turn are valuable starting materials for syntheses of penicillins and cephalosporins. Hitherto, these aminoacids have been prepared synthetically or biosynthetically. The synthetic method of preparation gives D,L-N-carbamyl-α-aminoacids, which must be separated into the antipodes. This separation is expensive and gives yields of at most 50%.

Optically pure carbamylaminoacids can be obtained by enzymatic cleavage of hydantoins, with the aid of a dihydropyrimidinase (German Laid-Open Application DOS No. 2,422,737). However, the reaction takes place relatively slowly and accordingly gives a poor space-time yield. Furthermore, only limited amounts of the enzyme are available.

According to German Laid-Open Application DOS No. 2,631,048, racemic mixtures of hydantoins can be converted to optically active aminoacids with the aid of micro-organisms of the species Pseudomonas. This reaction takes place at about 30° C. and only succeeds in relatively dilute solutions, so that once again the space-time yield is poor.

The present invention relates to a process for the preparation of D-carbamyl-α-aminoacids of the formula

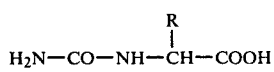

where R is alkyl of 1 to 4 carbon atoms, of which one hydrogen can be replaced by $NH_2$, OH or SH, or R is benzyl, of which one or two hydrogens can be replaced by OH, or R is phenyl, in which one or two hydrogens can be replaced by OH or $C_{1-4}$-alkoxy, by enzymatic hydrolysis of a hydantoin of the formula II

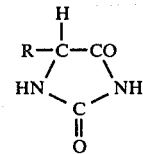

where R has the above meanings, wherein the enzymatic conversion is effected with the aid of thermophilic, non-sporulating, hydantoin-cleaving micro-organisms or of extracts obtained therefrom.

The invention further relates to thermophilic, non-sporulating, hydantoin-cleaving micro-organisms or extracts prepared therefrom, which are useful for the preparation of D-carbamyl-α-aminoacids from hydantoins.

The thermophilic, non-sporulating, hydantoin-cleaving micro-organisms can be obtained as follows:

Samples of water which is exposed to a relatively high temperature for a lengthy period—for example water from hot springs in Iceland or in Yellowstone Park (U.S.A.)—are drawn through a membrane filter. The filters are then placed on a nutrient agar which has been sterilized for 30 minutes at 121° C. and has the following composition:

| | |
|---|---|
| Castenholz mineral salt solution (Nature 215 (1967), 1285) | 1,000 ml |
| Yeast extract | 2.5 g |
| Tryptone | 2.5 g |
| Agar-agar | 30.0 g |
| Sodium hydroxide solution | to give pH 8.2 |

The colonies which grow on the membrane filter after incubation at 60° C. are isolated and transferred to a pure culture. To test the hydrantoin hydrolase activity, the thermophilic, non-sporulating bacteria thus obtained are incubated in a solution containing 10 g/l of $KH_2PO_4$, 75 ml/l of N NaOH and 10 g/l of methylthioethylhydantoin for 24 hours at 60° C. The individual reaction mixtures are examined for content of N-carbamylaminoacid. If the test is positive, the acid is isolated from the mixture and tested polarimetrically for optical purity. If it is found to be pure, the micro-organism concerned is classified as useful.

Two strains thus obtained have been deposited with the Centraal Bureau voor Schimmelcultures (CBS) in Baarn/Netherlands, under number 303.80 on 11.4.1980 and 363.80 and 4.8.1980. They have the following properties:

| | CBS 303.80 | CBS 363.80 |
|---|---|---|
| Colony morphology | red-pigmented, round colonies | red-pigmented, round colonies |
| Sporulation | negative | negative |
| Cell morphology | immobile thin rods | immobile rods |
| Oxygen conditions | compulsorily aerobic | compulsorily aerobic |
| Catalase | present | present |
| Oxidase | present | negative |
| Gram stain | gram-negative | gram-negative |
| Growth temperature | minimum 40° C., optimum 60° C. maximum slightly above 60° C. | 40–60° C. |
| Growth with: | sucrose, galactose, lactose | sucrose, glutamate, acetate, malate |
| No growth with: | glucose, xylose, glutamate, acetate, malate, succinate, glutarate | galactose, lactose, glucose, xylose, succinate, glutarate |
| Litmus milk | no degradation | no degradation, litmus reduction |
| Starch degradation | no degradation | no degradation |
| Casein degradation | negative | positive |
| Growth in 3% NaCl | negative | negative |

| CBS 303.80 | CBS 363.80 |
|---|---|
| broth | |

Examples of 5-substituted hydantoins which can be hydrolyzed to N-carbamyl-D-aminoacids by the bacteria according to the invention are listed in Table 1.

TABLE 1

| Substrate | Product |
|---|---|
| 5-methylhydantoin | D-N—carbamylalanine |
| 5-ethylhydantoin | D-N—carbamyl-α-aminobutyric acid |
| 5-(2-methyl-thioethyl)-hydantoin | D-N—carbamylmethionine |
| 5-benzylhydantoin | D-N—carbamylphenylalanine |
| 5-phenylhydantoin | D-N—carbamylphenylglycine |
| 5-(p-hydroxyphenyl)-hydantoin | D-N—carbamyl-p-hydroxyphenyl-glycine |
| 5-(p-methoxyphenyl)-hydantoin | D-N—carbamyl-p-methoxyphenyl-glycine |
| 5-(p-t-butoxyphenyl)-hydantoin | D-N—carbamyl-p-t-butoxyphenyl-glycine |
| 5-(p-acetoxyphenyl)-hydantoin | D-N—carbamyl-p-acetoxyphenyl-glycine |

The process according to the invention is preferably carried out at from 40° to 90° C. and at a pH of from 7 to 10. To carry out the process, the bacteria according to the invention or mutants derived therefrom can be used in a free or immobilized form. Extracts of the micro-organisms can also be employed. The extracts can be prepared, for example, as follows:

A cell suspension in buffer is treated with ultrasonics at from 5 to 10 minutes, whilst cooling with ice. After centrifuging off the cell fragments, the hydantoin-cleaving enzyme is found to be in solution in the supernatant liquor. The latter can be employed direct, as the crude extract, for the process according to the invention.

The process according to the invention, and the novel micro-organisms, have the following advantages:

1. The culturing of non-sporulating thermophilic micro-organisms is simpler than that of sporulating thermophilic micro-organisms (for example species of Bacillus cf. German Laid-Open Application DOS No. 2,811,303), since, in the case of the latter, the fermentation must be stopped before sporulation occurs. With the micro-organisms according to the invention, there is no danger of sporulation, and enzymatically active cells are present at all times.

2. The cell yield is higher for non-sporulating organisms than for the corresponding sporulating organisms.

3. The thermophilic, non-sporulating bacteria make it possible to carry out the reaction at higher temperatures than those described in the literature. This has several advantages:
   (a) greater solubility of the hydantoins,
   (b) more rapid post-racemization of the hydantoins and
   (c) more rapid enzymatic conversion of the hydantoins to the D-carbamylaminoacids.

4. The thermophilic non-sporulating strains employed for the hydantoin hydrolysis tolerate substantially higher substrate concentrations than do the organisms described hitherto. Accordingly, the space-time yields are higher.

EXAMPLE 1

Three 1 liter Erlenmeyer flasks each containing 170 ml of sterile medium (composition: Castenholz mineral salt solution (Nature 215 (1967), 1285), 0.258 g/l of $Na_3PO_4.12H_2O$, 10 g/l of yeast extract and 2.5 g/l of tryptone, pH 7.0) are inoculated with slant agar cultures of the strain CBS 303.80 and incubated for 46 hours at 60° C., whilst shaking at 200 rpm.

A fermenter containing 20 liters of sterile medium of the above composition and 5 ml of anti-foam agent is then inoculated with these 3 pre-cultures. Fermentation is carried out under the following conditions:
Temperature: 60° C.
pH: 7.0, maintained by adding 2 M $H_3PO_4$
Aeration: 0.1 VVM of air
Speed of stirring: 500 rpm After a fermentation time of 25.5 hours, 1 liter of the culture broth (containing 11.4 g of moist bacterial mass) is taken, 1 g of polyoxyethylene-20 cetyl ether and 17.6 g of 5-phenylhydantoin are added and the incubation is continued under the following conditions:
Temperature: 60° C.
pH: 8.5, maintained by adding 5 N NaOH
Aeration: 0.1 VVM of nitrogen
Speed of stirring: 200 rpm After an incubation time of 7 hours, the batch is centrifuged and the D-N-carbamylphenylglycine is precipitated by acidifying the supernatant liquor to pH 2.5 with 10% strength HCl.

After recrystallization from acetone, the specific rotation $[\alpha]_D^{20°}$ C.$= -138.8°$ (C=1 in 1 M $NH_3$), and the melting point is 193° C.

EXAMPLE 2

The strain CBS 303.80 is cultured as described in Example 1, but whilst culturing the cell mass the speed of stirring and aeration are regulated so that the $O_2$ concentration in the nutrient medium is at all times 10% of the maximum value achievable by aeration with air. After a fermentation time of 23 hours, the cell mass is isolated by centrifuging and the supernatant liquor is discarded.

50 g of moist cell mass are suspended in 1 liter of medium of the following composition: 2 g/l of $KH_2PO_4$, 100 g/l of 5-phenylhydantoin and 1 g/l of demineralized water. The pH is brought to 8.5, and kept constant, with 5 N NaOH. The batch is heated to 60° C., stirred at 300 rpm and gassed with 0.1 VVM of $N_2$.

After 5 hours, the yield of N-carbamylphenylglycine is 94.5%. The batch is worked up as in Example 1. The reaction product is once again optically pure D-N-carbamylphenylglycine.

EXAMPLE 3

Cell mass of the strain CBS 303.80 is isolated as in Example 2 and then dried to constant weight under reduced pressure at 40° C. 5.75 g of this dry cell powder are incubated in 500 ml of medium containing 2 g/l of $KH_2PO_4$ and 100 g/l of 5-phenylhydantoin, as in Example 2. The yield of optically pure D-N-carbamylphenylglycine, after 6 hours, is 86%.

EXAMPLE 4

25 g of moist cell mass of the strain CBS 303.80, obtained as described in Example 2, are suspended in 500 ml of the medium described in Example 2, subjected to ultrasonics (20 kHz) for 9 minutes at 4° C. and then incubated at 60° C., with stirring at 300 rpm, at pH 8.5, whilst passing 0.1 VVM of $N_2$. The yield of optically pure D-N-carbamoylphenylglycine, after 6 hours, is 69%.

EXAMPLE 5

25 g of moist cell mass of the strain CBS 303.80, obtained as described in Example 2, are incubated in 500 ml of a medium of the following composition, at 60° C., whilst stirring at 300 rpm, at pH 8.5, and whilst passing 0.1 VVM of $N_2$: 50 g of 5-phenylhydantoin, 1 g of $KH_2PO_4$, 0.5 g of polyoxyethylene-20 cetyl ether, demineralized water to make up to 500 ml.

The yield of optically pure D-N-carbamylphenylglycine, after 7 hours, is 86%.

EXAMPLE 6

60 g of moist cell mass, prepared as described in Example 2, are suspended in 1 liter of medium of the following composition: 10 g/l of $KH_2PO_4$, 1 g/l of polyoxyethylene-20 cetyl ether and 50 g/l of 5-(p-methoxyphenyl)-hydantoin.

The reaction is carried out under the following conditions: temperature 60° C., pH 8.5, kept constant by adding 5 M NaOH, 0.1 VVM of $N_2$.

After 22 hours, the experiment is stopped and the D-N-carbamyl-p-methoxyphenylglycine formed is isolated as in Example 1. Yield: 92%, melting point: 212°–213° C., $[\alpha]_D^{20°}$ C. $= -138.7$ (C=1 in 1 M $NH_3$).

The properties of the compound are identical with those of D-N-carbamyl-p-methoxyphenylglycine.

EXAMPLE 7

20 g of moist cell mass of the strain CBS 303.80, obtained as described in Example 2, are incubated in 500 ml of a medium of the following composition, at 60° C., whilst stirring at 300 rpm, at pH 8.5, and whilst passing 0.1 VVM of $N_2$: 20 g of p-tert.-butoxyphenylhydantoin, 1 g of $KH_2PO_4$, 0.5 g of polyoxyethylene-20 cetyl ether, demineralized water to make up to 500 ml.

The yield of optically pure N-carbamyl-D-p-tert.-butoxyphenylglycine, after 26 hours, is 39%.

EXAMPLE 8

20 g of moist cells mass of the strain CBS 303.80, obtained as described in Example 2, are incubated in 500 ml of a medium of the following composition, at 60° C., whilst stirring at 300 rpm, at pH 8.5, and whilst passing 0.1 VVM of $N_2$: 10 g of 5-benzylhydantoin, 1 g of $KH_2PO_4$, 0.5 g of polyoxyethylene-20 cetyl ether, deionized water to make up to 50 ml.

The yield of optically pure N-carbamyl-D-phenylalanine, after 25.5 hours, is 30%.

EXAMPLE 9

0.9 g of moist cell mass of the strain CBS 363.80, obtained as described in Example 2, is incubated in 100 ml of a medium of the following composition, at 60° C., and pH 8.77: 0.5 g of 5-methylthioethylhydantoin, 7 g of $K_2HPO_4$, demineralized water to make up to 100 ml.

The yield of optically pure N-carbamyl-D-methionine, after 48 hours, is more than 90%.

EXAMPLE 10

20 g of 5-methylthioethylhydantoin are reacted with 25 g of moist cell mass under the conditions described in Example 8. The yield of optically pure N-carbamyl-D-methionine, after 6 hours, is 87.7%.

EXAMPLE 11

A 20% strength (moist weight) suspension of cells, which have been cultured as described in Example 2, in 0.2 M tris/HCl, pH 8.0, was treated with ultrasonics for 3 periods of 3 min. After centrifuging (at 10,000 g), 72 ml of the supernatant liquor were mixed with 18 ml of a 1% strength aqueous solution of cetylpyridinium chloride. The centrifugate from this precipitation step constitutes the hydrantoinase crude preparation used for the reaction. The reaction was carried out under the following conditions: 90 ml of hydantoinase crude preparation, 410 ml of demineralized water, 50 g of phenylhydantoin, pH 8.5 (adjusted with NaOH), 60° C., 300 rpm, gassing with $N_2$.

The yield of optically pure D-N-carbamylphenylglycine, after 24 hours, was 94.1%.

EXAMPLE 12

100 ml of a hydantoinase crude preparation prepared as in Example 11 were diluted with 100 ml of demineralized water and shaken, at 4° C., with 30 g of moist DE-52 cellulose (Whatman; equilibrated with 100 mM tris/HCl, pH 8.0). After 2 hours, the entire hydantoinase activity had been adsorbed on the ion exchanger; the latter was filtered off and washed with 50 ml of 50 mM tris/HCl, pH 8.0; no hydantoinase activity was detectable in the wash water. This carrier-fixed crude preparation was incubated with 50 g of phenylhydantoin in 450 ml of demineralized water at pH 8.5 and 60° C., whilst gassing with $N_2$. The yield of optically pure D-N-carbamylphenylglycine, after 6.5 hours, was 94.9%.

EXAMPLE 13

60 $\mu$l of tetramethylethylenediamine and 2 ml of a 10% strength aqueous $(NH_4)_2S_2O_8$ solution were added to a suspension of 7.5 g of acrylamide, 0.4 g of N,N'-methylene-bis-acrylamide and 10 g of moist cell mass from Example 2 in 50 ml of physiological sodium chloride solution, whilst gassing with $N_2$, and the mixture was left to stand at room temperature for 30 minutes. The gel thus formed was comminuted in a mixer and then washed with 5 times 100 ml of physiological sodium chloride solution. The treated gel particles were suspended in 600 ml of water containing 1 g of $KH_2PO_4$ and 10 g of 5-phenylhydantoin. The yield of N-carbamyl-D-phenylglycine, after 6.5 hours, was 97.3%. A further 30 g of phenylhydantoin were added to the solution. After a further 15.5 hours the yield was 94.5%.

EXAMPLE 14

Cell mass of strain CBS 303.80, cultured as described in Example 2, was incubated for 30 minutes, at 40°, 50°, 60°, 70°, 80° or 90° C., in the following buffer: 10 g/l of $KH_2PO_4$, 1 g/l of polyoxyethylene-20 cetyl ether, 10 g/l of methylthioethylhydantoin and 10 g/l of dry bacterial mass, pH adjusted to 8.5 with NaOH. The content of N-carbamyl-D-methionine was then determined.

| Temperature (°C.) | Yield of N—carbamyl-D-methionine (%) |
|---|---|
| 40 | 43.4 |
| 50 | 48.0 |

-continued

| Temperature (°C.) | Yield of N—carbamyl-D-methionine (%) |
| --- | --- |
| 60 | 55.9 |
| 70 | 61.4 |
| 80 | 70.6 |
| 90 | 34.1 |

EXAMPLE 15

Cell mass from Example 2 was incubated for 30 minutes at 60° C. and at a pH of from 7.0 to 10 in the following buffer, (the pH being kept at the desired value by dosed addition of NaOH): 10 g/l of methylthioethyl-hydantoin, 10 g/l of $KH_2PO_4$, 1 g/l of polyoxyethylene-20 cetyl ether and 10 g/l of dry bacterial mass. The yield of N-carbamyl-D-methionine was found to depend on the pH as follows:

| pH | Yield of N—carbamyl-D-methionine (%) |
| --- | --- |
| 7.0 | 46.5 |
| 7.5 | 48.5 |
| 8.0 | 55.2 |
| 8.5 | 58.0 |
| 9.0 | 51.7 |
| 9.5 | 50.7 |
| 10.0 | 22.3 |

EXAMPLE 16

2.5 ml of a hydantoinase crude preparation prepared as described in Example 11 were diluted with 60 ml of water. 300 mg of p-hydroxyphenylhydantoin were added to the mixture and the batch was stirred at 60° C., whilst gassing with $N_2$ and keeping the pH at 8.0 by adding 1 N sodium hydroxide solution. The yield of optically pure N-carbamyl-p-hydroxy-D-phenylglycine, after 18 hours, was 92%.

We claim:

1. A process for the preparation of a D-carbamyl-α-aminoacid of the formula I

where R is alkyl of 1 to 4 carbon atoms, of which one hydrogen can be replaced by $NH_2$, OH, —$SCH_3$ or SH, or R is benzyl, of which one or two hydrogens can be replaced by OH, or R is phenyl, in which one or two hydrogens can be replaced by OH, acetoxy or $C_{1-4}$-alkoxy, by enzymatic hydrolysis of a hydantoin of the formula II

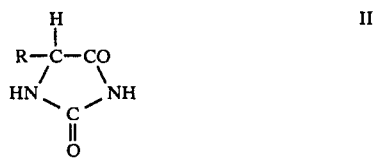

where R has the above meanings, wherein the enzymatic conversion is effected with the aid of the thermophilic, non-sporulating, hydantoin-cleaving microorganisms CBS 303.80 or CBS 363.50 or of extracts obtained therefrom.

2. A pure culture of the thermophilic, non-sporulating microorganism CBS 303.80.

3. A pure culture of the thermophilic, non-sporulating microorganism CBS 363.50.

4. A crude extract of the microorganism of claim 2 or 3.

5. A hydantoin-cleaving extract of the microorganism of claim 2 or 3.

* * * * *